Figure 1:
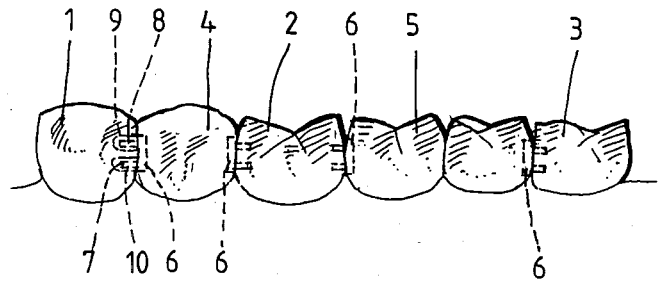

United States Patent [19]

Jansen

[11] Patent Number: 4,583,948
[45] Date of Patent: Apr. 22, 1986

[54] APPARATUS FOR CONNECTING DENTAL PROSTHESES

[75] Inventor: Jozef Jansen, Rotterdam, Netherlands

[73] Assignee: Elgarden Aktiengesellschaft, Vaduz, Liechtenstein

[21] Appl. No.: 637,731

[22] Filed: Aug. 6, 1984

[30] Foreign Application Priority Data

Apr. 27, 1984 [CH] Switzerland .......................... 2090/84

[51] Int. Cl.$^4$ ............................................. A61C 13/22
[52] U.S. Cl. ................................................... 433/181
[58] Field of Search ................. 433/181, 182, 191, 192

[56] References Cited

FOREIGN PATENT DOCUMENTS

| 352782 | 4/1961 | Switzerland | 433/181 |
| 2085303 | 4/1982 | United Kingdom | 433/181 |
| 2117643 | 10/1983 | United Kingdom | 433/181 |
| 2117642 | 10/1983 | United Kingdom | 433/181 |

*Primary Examiner*—John J. Wilson
*Attorney, Agent, or Firm*—Stevens, Davis, Miller & Mosher

[57] ABSTRACT

The apparatus comprises an anchoring element having a lower recess and a continuous upper recess. Pins are rotatably and swivellably mounted in the recesses. The pins comprise a cylindrical portion and a spherical portion. The anchoring element is preferably first cemented with the lower pin into a hole drilled in an existing supporting tooth, whereupon a second hole in this tooth can then be drilled through the upper continuous opening in the anchoring element for receiving the upper pin. Thus, there is no need to drill exactly spaced, parallel holes in the supporting teeth, nor is there any necessity for a drilling template.

8 Claims, 9 Drawing Figures

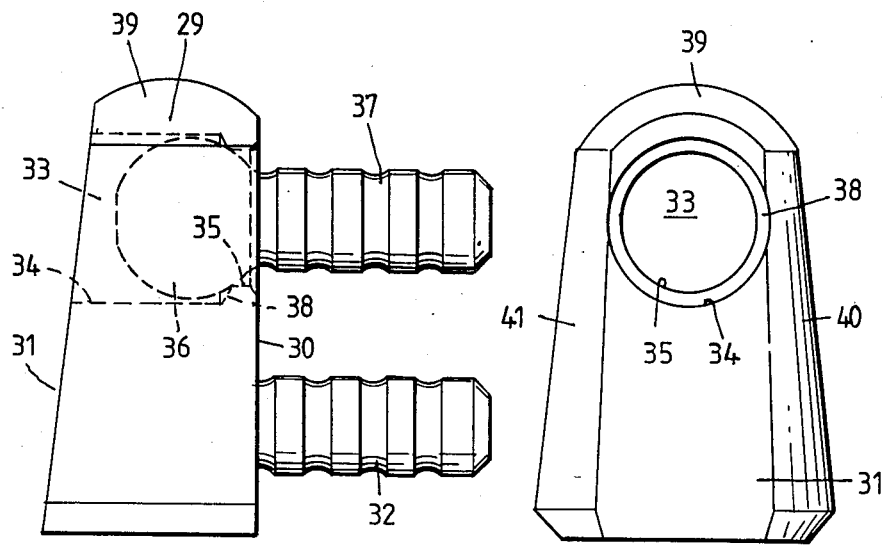
FIG. 6
FIG. 8
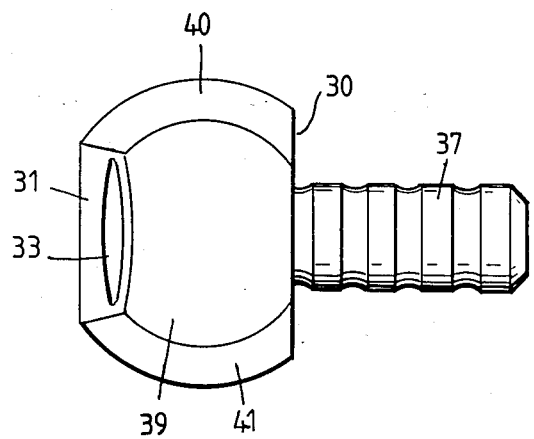
FIG. 7
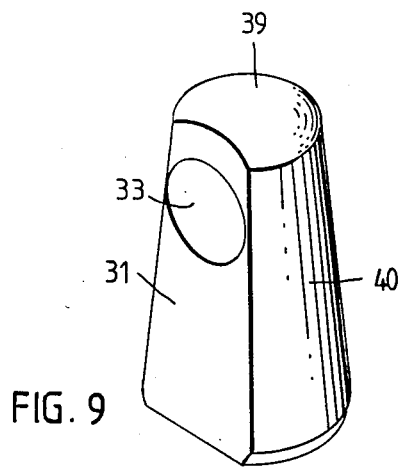
FIG. 9

APPARATUS FOR CONNECTING DENTAL PROSTHESES

This invention relates to dental prostheses, and in particular to apparatus for connecting such prostheses, of the type having at least one anchoring element with at least two recesses for receiving pins intended to engage existing teeth or supports, as well as to a pin for use with the apparatus.

European Patent Application Publication No. 0 025 419 discloses apparatus for connecting dental prostheses comprising anchoring elements having two pins insertable in the teeth bounding a tooth gap. A drawback of this apparatus is that the two pins are fixed to a retaining plate. Therefore, when corresponding holes are drilled in the teeth bounding the gap, it is necessary to drill two parallel holes with great precision, which meets with considerable difficulty in practice.

Hence it is an object of this invention to provide improved apparatus for connecting dental prostheses which do not have that drawback.

To this end, in the apparatus according to the present invention, of the type initially described, the improvement comprises at least one pin which can be pivotingly mounted in the recess intended for it.

The pin according to the present invention is cylindrical and includes a spherical portion.

One advantage of the apparatus according to this invention is that the holes for receiving the pins in the teeth serving as supports can be drilled in different directions, and two holes drilled into the tooth need not be parallel. Furthermore, in contrast to the prior art apparatus, no drilling templates are necessary.

Two preferred embodiments are designed for use in the area of the incisors and in the molar region, respectively. In the incisor embodiment, the outside surface of the anchoring element is at least partially of cylindrical shape but is planar in the region where the pins project from it. The embodiment for use in the molar region is substantially conical, the supporting surface of the anchoring element being enlarged since greater forces occur in that region.

Figure 4:
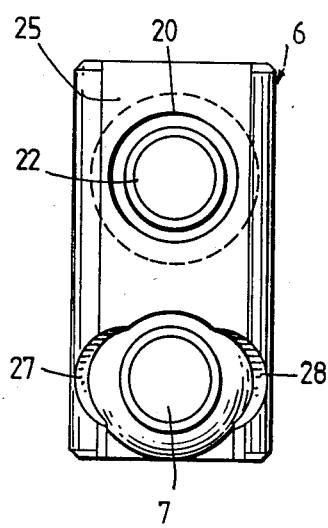
Figure 2:
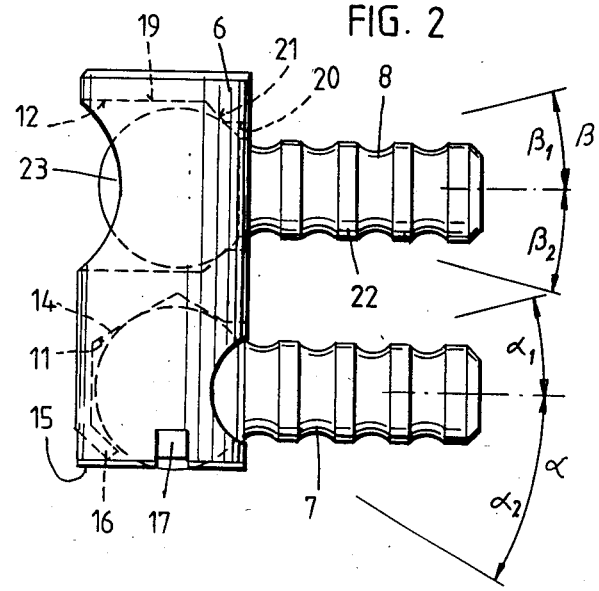
Figure 5:
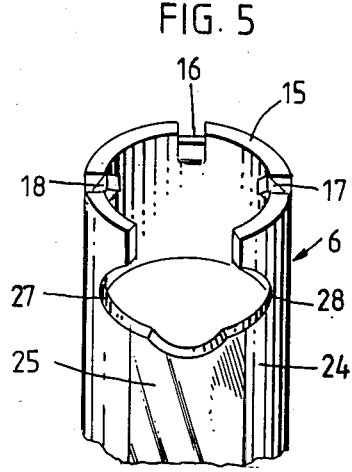
Figure 3:
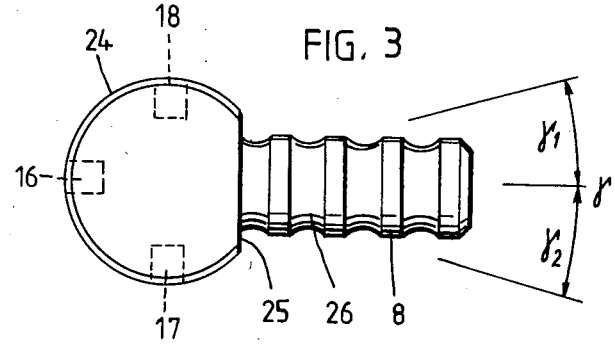

Other objects and advantages of the invention will become apparent from the following detailed description of preferred embodiments thereof and their use, taken in conjunction with the accompanying drawings, in which:

FIG. 1 is a diagrammatic perspective view intended to make plain the use of the apparatus for connecting dental prostheses, FIG. 2 is a side elevation of a first embodiment of the invention, FIG. 3 is a top plan view of the embodiment of FIG. 2, FIG. 4 is a front elevation of the embodiment of FIGS. 2 and 3, FIG. 5 is a perspective view from below of the first embodiment, FIG. 6 is a side elevation of a second embodiment of the invention, FIG. 7 is top plan view of the second embodiment, FIG. 8 is an elevation of the second embodiment, and FIG. 9 is a perspective view of the anchoring element of the second embodiment.

In FIG. 1, the use of the apparatus for connecting dental prostheses is illustrated diagrammatically. Three existing teeth 1, 2, and 3 bound two tooth gaps into wihch prostheses 4 and 5 are inserted. Anchoring elements 6 are secured in existing teeth 1, 2, and 3 by means of pins 7 and 8 cemented into respective holes 9 and 10 drilled in the existing fixed teeth.

Prostheses 4 and 5 are secured to anchoring elements 6. Both these elements and pins 7 and 8 are preferably made of titanium.

In FIG. 2, illustrating a first embodiment of the invention, the apparatus for connecting dental prostheses is seen to comprise an anchoring element 6 and two pins 7 and 8 to be inserted into existing teeth, these pins being pivotingly and swivellingly connected to element 6. Anchoring element 6 includes a lower recess 11 and an upper recess 12. Recess 11 is in the form of a blind bore having a conical bottom 14 and a rim 15 provided with three catches 16, 17, and 18. Upper recess 12 is continuous and consists of two cylindrical parts 19 and 20 separated by a beveled shoulder 21. Pins 7 and 8 are identical, each having a cylindrical portion 22 and a spherical portion 23. Lower pin 7 is held pivotably and swivellably in lower recess 11 by means of catches 16, 17, and 18. Cylindrical portion 22 of upper pin 8 is inserted first through the larger cylindrical part 19 of recess 12, then through the second cylindrical part 20 of smaller diameter, so that spherical portion 23 of pin 8 rests against shoulder 21 and is likewise pivotably and swivellably mounted in upper recess 12. Pin 7 is swivellably mounted in a vertical plane about an angle $\alpha$ and pin 8 about an angle $\beta$. Lower pin 7 can be swivelled downward through an angle $\alpha_1$ (30°) and upward through the smaller angle $\alpha_2$ (15°). Upper pin 8 can be swivelled downward and upward through an angle $\beta_1$ (15°).

It will be seen from FIG. 3 that the portion of anchoring element 6 where the prosthesis is affixed takes the form of a cylindrical shell 24. In the region designated by reference numeral 25, where the cylindrical portions of pins 7 and 8 project from element 6, i.e., toward the tooth serving as a support, element 6 is flat. Pins 7 and 8 are provided with grooves 26. In the horizontal plane, upper pin 8 is swivelable through an angle $\gamma$ (30°), i.e., through an angle $\gamma_1$ (15°) to each side.

In FIG. 4, the first embodiment of the apparatus is illustrated from the front, i.e., looking from cylindrical portions 22 of pins 7 and 8 toward anchoring element 6. In the vicinity of lower pin 7 there are lateral recesses 27 and 28 which make it possible to swivel lower pin 7 in the horizontal plane through a large angle than upper pin 8.

In FIG. 5, showing the anchoring element from below, the three catches 16–18 may be seen. These are produced by notching rim 15 of cylindrical shell 24 and are bent in slightly in order to hold spherical portion 23 of pin 7 in lower recess 11.

A second embodiment of the invention is shown in elevation in FIG. 6. An anchoring element 29 is flat in the region designated by reference numeral 30, where the cylindrical portions of pins 32 and 37 project from the prosthesis toward the tooth serving as a support, and the opposite surface 31 of element 29 is also flat. A lower recess (not visible) is blind, as in the first embodiment, pin 32 also being held therein in the same way as described with reference to FIGS. 2–5. Upper recess 33 includes two cylindrical parts 34 and 35 of differing diameters and is continuous. The spherical portion 36 of upper pin 37 rests against a shoulder 38 joining cylindrical parts 34 and 35. The top 39 of element 29 is rounded.

FIGS. 7, 8, and 9 are a top plan view, a front elevation, and a perspective view, respectively, of the second embodiment, from which it may be seen that the two surfaces of anchoring element 29 joining flat surfaces 30 and 31 have a conical-shell shape. The last two drawing figures show element 29 alone, without pins. Anchoring element 6, 29 is preferably first cemented with lower pin 7, 32 into a lower hole drilled in the tooth. A second hole is then drilled in the tooth, preferably through continuous upper recess 12, 13 in the anchoring element, for receiving upper pin 8, 37. The anchoring element can be swivelled about the cemented-in lower pin. Because of the additional swivelling possibility of the upper pin, the two holes drilled need not be parallel.

With the described apparatus for connecting dental prostheses, it is also no longer necessary to grind down sound teeth for the purpose of putting in bridges, for example.

What is claimed is:

1. Apparatus for connecting dental prostheses, comprising two pins intended to engage existing teeth or supports, at least one anchoring element including two or more recesses for respectively receiving said two pins, and means for mounting at least one of said pins pivotingly in the associated one of said recesses, at least one of said recesses being a continuous throughbore disposed substantially perpendicular to a longitudinal axis of the anchoring element for enabling a hole to be drilled in the tooth through the anchoring element.

2. The apparatus of claim 1, further including means for holding one of said pins in the associated one of said recesses.

3. The apparatus of claim 1, wherein said pins project from said anchoring element, said anchoring element being made flat in the vicinity of the point of exit of said pins.

4. The apparatus of claim 1, wherein the outside surface of said anchoring element is at least partially cylindrical.

5. The apparatus of claim 1, wherein said anchoring element has a substantially conical shape.

6. The apparatus of claim 5, wherein the outside surface of said anchoring element is at least partially of a conical-shell shape.

7. The apparatus of claim 1, wherein at least one said pin comprises a cylindrical portion and a spherical portion, said cylindrical portion allowing a tooth to contact said anchoring element.

8. The apparatus of claim 7, wherein said cylindrical portion is provided with grooves.

* * * * *